United States Patent
Wright et al.

(10) Patent No.: US 12,150,719 B2
(45) Date of Patent: Nov. 26, 2024

(54) SURGICAL SUPPORT SYSTEM, DATA PROCESSING APPARATUS AND METHOD

(71) Applicant: Sony Corporation, Tokyo (JP)

(72) Inventors: Christopher Wright, London (GB); Matthew Lawrenson, Lausanne (CH); Bernadette Elliott-Bowman, London (GB); Taro Azuma, Tokyo (JP)

(73) Assignee: Sony Corporation, Tokyo (JP)

( * ) Notice: Subject to any disclaimer, the term of this patent is extended or adjusted under 35 U.S.C. 154(b) by 873 days.

(21) Appl. No.: 17/281,588

(22) PCT Filed: Sep. 27, 2019

(86) PCT No.: PCT/JP2019/038339
§ 371 (c)(1),
(2) Date: Mar. 31, 2021

(87) PCT Pub. No.: WO2020/075545
PCT Pub. Date: Apr. 16, 2020

(65) Prior Publication Data
US 2021/0386489 A1    Dec. 16, 2021

(30) Foreign Application Priority Data
Oct. 12, 2018   (EP) .................................... 18200261

(51) Int. Cl.
*A61B 34/00*        (2016.01)
*A61B 90/00*        (2016.01)
(Continued)

(52) U.S. Cl.
CPC .............. *A61B 34/25* (2016.02); *A61B 90/37* (2016.02); *A61B 90/50* (2016.02); *G06N 5/043* (2013.01);
(Continued)

(58) Field of Classification Search
None
See application file for complete search history.

(56) References Cited

U.S. PATENT DOCUMENTS

| 2013/0073387 A1 | 3/2013 | Heath |
| 2014/0081659 A1 | 3/2014 | Nawana et al. |

(Continued)

FOREIGN PATENT DOCUMENTS

| AU | 2008100920 A4 | 10/2008 |
| CN | 104363826 A | 2/2015 |

(Continued)

OTHER PUBLICATIONS

International Search Report and Written Opinion mailed on Dec. 10, 2019, received for PCT Application PCT/JP2019/038339, filed on Sep. 27, 2019, 13 pages.
(Continued)

*Primary Examiner* — Eric Nilsson
(74) *Attorney, Agent, or Firm* — XSENSUS LLP

(57) ABSTRACT

A surgical support system including: a surgical data generating apparatus operable to generate surgical data associated with a surgical procedure; and a data processing apparatus operable to: determine artificial intelligence (AI) assistance information using the generated surgical data; and provide the determined AI assistance information to a user.

20 Claims, 6 Drawing Sheets

(51) Int. Cl.
*A61B 90/50* (2016.01)
*G06N 5/043* (2023.01)
*G06N 20/00* (2019.01)
*G16H 20/40* (2018.01)

(52) U.S. Cl.
CPC ............. *G06N 20/00* (2019.01); *G16H 20/40* (2018.01); *A61B 2090/502* (2016.02)

(56) References Cited

U.S. PATENT DOCUMENTS

| | | | |
|---|---|---|---|
| 2015/0282796 | A1 | 10/2015 | Nawana |
| 2017/0199189 | A1* | 7/2017 | Wade ............... G01N 33/56955 |
| 2017/0367766 | A1 | 12/2017 | Mahfouz |
| 2017/0367771 | A1* | 12/2017 | Tako ..................... G16H 20/40 |
| 2018/0032698 | A1 | 2/2018 | Lau |
| 2018/0065248 | A1* | 3/2018 | Barral ................... G06N 20/00 |

FOREIGN PATENT DOCUMENTS

| | | |
|---|---|---|
| CN | 105636541 A | 6/2016 |
| CN | 106030683 A | 10/2016 |
| CN | 107078754 A | 8/2017 |
| CN | 107613897 A | 1/2018 |
| CN | 108472084 A | 8/2018 |
| WO | 2017/220788 A1 | 12/2017 |

OTHER PUBLICATIONS

Mezger et al., "Navigation in Surgery", Langenbeck's Archives of Surgery, vol. 398, No. 4, Feb. 22, 2013, pp. 501-514.

* cited by examiner

FIG.2A

| Procedure Type / Stage | Expertise Data | AI ID |
|---|---|---|
| Heart transplant / Stage 1 (manual incision) | Incision technique | AI 1, AI 2, AI 3 |
| Heart transplant / Stage 1 (manual incision) | Incision length | AI 1, AI 2, AI 3 |
| Heart transplant / Stage 2 (blood vessel attachment) | Attachment equipment | AI 3, AI 5, AI 6 |
| Heart transplant / Stage 2 (blood vessel attachment) | Damage avoidance | AI 5, AI 6, AI 7 |
| Heart transplant / Stage 2 (blood vessel attachment) | Attachment success | AI 3, AI 5, AI 6 |
| Heart transplant / Stage 3 (robot incision) | Incision planning | AI 1, AI 7, AI 8 |

FIG.2B

| AI ID | Requester Relationship Score |
|---|---|
| AI 3 | 2 |
| AI 5 | 8 |
| AI 6 | 9 |

FIG.2C

| AI ID | Advice Value Score | Training Quality Score |
|---|---|---|
| AI 3 | 7 | 10 |
| AI 5 | 7 | 5 |
| AI 6 | 5 | 9 |

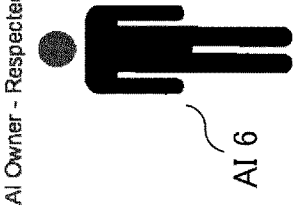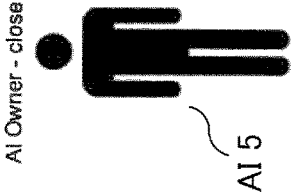
FIG.3

FIG.4A

| Procedure Type / Stage | Expertise Data | Relevant Team Members | AI ID |
|---|---|---|---|
| Heart transplant / Stage 1 (manual incision) | Incision technique | Surgeon Camera Operator | AI 1, AI 2, AI 3 |
| Heart transplant / Stage 1 (manual incision) | Incision length | Surgeon | AI 1, AI 2, AI 3 |
| Heart transplant / Stage 2 (blood vessel attachment) | Attachment equipment | Surgeon Camera Operator Nurse | AI 3, AI 5, AI 6 |
| Heart transplant / Stage 2 (blood vessel attachment) | Damage avoidance | Surgeon Nurse | AI 5, AI 6, AI 7 |
| Heart transplant / Stage 2 (blood vessel attachment) | Attachment success | Surgeon | AI 3, AI 5, AI 6 |
| Heart transplant / Stage 3 (robot incision) | Incision planning | Surgeon | AI 1, AI 7, AI 8 |

FIG.4B

| Team Member | Member ID | Preferred AI ID | Other Preference |
|---|---|---|---|
| Surgeon | Member 1 | AI 3 | Monitor visualisation style = X |
| Camera Operator | Member 2 | AI 5 | Machine alert type = audible only |
| Nurse | Member 3 | AI 3 | N/A |

SURGICAL SUPPORT SYSTEM, DATA PROCESSING APPARATUS AND METHOD

CROSS-REFERENCE TO RELATED APPLICATIONS

The present application is based on PCT filing PCT/JP2019/038339, filed Sep. 27, 2019, which claims priority to EP 18200261.8, filed Oct. 12, 2018, the entire contents of each are incorporated herein by reference.

TECHNICAL FIELD

The present disclosure relates to a surgical support system, data processing apparatus and method.

BACKGROUND

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

Humans within an operating theatre context may require advice on decisions, such as surgical procedure advice for a surgeon and technical or medical advice for support staff such as camera operators, nurses, technicians and the like. This advice may be in the form of a second opinion, i.e. subjective advice from a respected colleague on a particular topic, or may be objective information about known best practice.

Although subjective advice from a colleague can be highly useful in situations which have no clear best practice, or where a best practice recommendation is not trusted, the availability of the colleague and the time taken to retrieve the advice can limit the utility of this option.

The utility of subjective advice is further limited by the value of the colleague's opinion, such as their degree of experience with the topic as well as their likelihood to challenge or provide differing input to the views of the advice seeker. Obtaining a diverse range of opinions not only introduces the advice seeker to other approaches that may not have been considered, but also triggers more careful information processing. However, while an individual who is only distantly associated with the advice requester is more likely to provide a differing opinion, they may also be less trusted by the requester.

Furthermore, there is a trade-off in the decision-making process of groups of individuals between 'groupthink', where diversity of opinion is low and optimal decisions may not be reached, and teamwork/efficiency, where decisions are reached quickly and efficiently due to the shared opinions.

There is therefore a need for a more effective way for operating theatre staff to be able to share relevant information with each other, especially when engaged in a surgical procedure (when the operating theatre staff having access to high quality, relevant information from colleagues will be particularly beneficial to the patient. In particular, there is a need to enable operating theatre staff to acquire subjective advice on unfamiliar scenarios within a highly time-constrained surgical environment. There is a need to alleviate the occurrence of confirmation bias and sub-optimal surgical decision-making resulting from the tendency for an individual to be exposed to and seek the opinions of people who agree with them. There is a need to alleviate the waste of potentially useful advice that may occur as a result of an advice requester's perceptions of an unknown or negatively perceived individual. There is a need to select and optimise the value of advice contributing to a decision which may be acquired rapidly from a large pool of knowledgeable individuals. There is also a need to alleviate a lack of trust between a human surgeon and technology in surgical decision-making.

SUMMARY

The present disclosure is defined by the claims.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings, wherein:

FIG. 2A schematically shows first example data used by the surgical support system in determining suitable artificial intelligence (AI) assistance information, according to an embodiment;

FIG. 2B schematically shows first example data used by the surgical support system in determining suitable artificial intelligence (AI) assistance information, according to an embodiment;

FIG. 2C schematically shows first example data used by the surgical support system in determining suitable artificial intelligence (AI) assistance information, according to an embodiment;

FIG. 3 schematically shows the determination of suitable AI assistance information based on scores attributed to different personal AIs, according to an embodiment;

FIG. 4A schematically shows second example data used by the surgical support system in determining suitable artificial intelligence (AI) assistance information, according to an embodiment;

FIG. 4B schematically shows second example data used by the surgical support system in determining suitable artificial intelligence (AI) assistance information, according to an embodiment;

DESCRIPTION OF EMBODIMENTS

Figure 1:
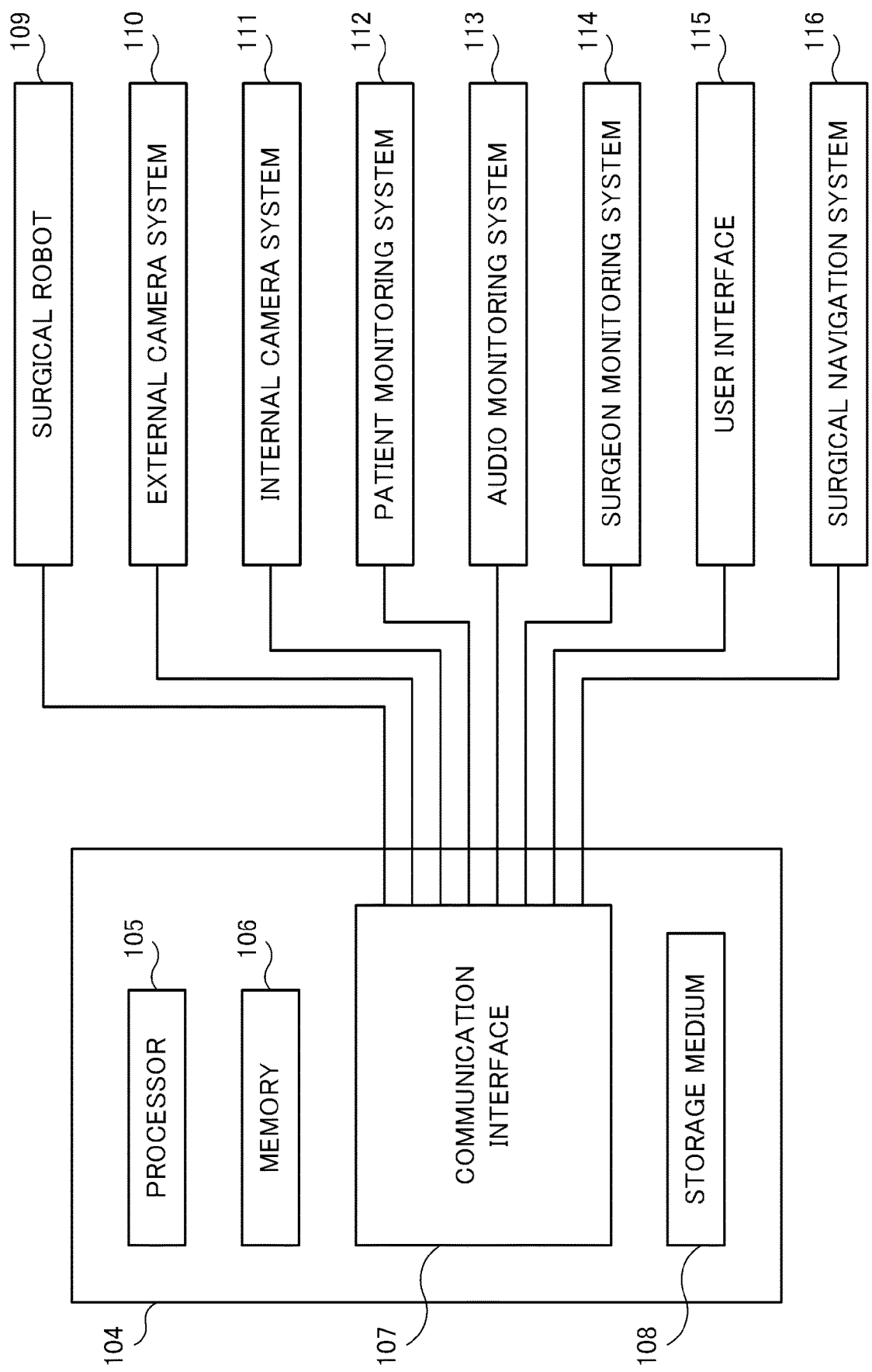
FIG. 1 schematically shows a surgical support system, according to an embodiment.

Referring now to the drawings, wherein like reference numerals designate identical or corresponding parts throughout the several views.

Personal AI assistants (also known as a personal AIs or AI assistants) use (i) one or more algorithms and (ii) data indicative of a person's decisions in known past situations to predict what decision that person would make in a known future situation. The more past data the AI assistant has access to, the more accurate the AI assistant's predictions will be. Such technology can be seen in "chat bots", for example, which are able to write posts or hold conversations in the style of an individual. Other examples include music or purchase recommendation platforms. As this technology improves, it will increasingly be employed for more professional purposes, such as providing a "virtual specialist" for medical consultation purposes. A personal AI assistant may comprise an intelligent agent which gathers information about its environment (through one or more sensors) and acts upon its environment (though one or more actuators) based on the gathered information. The action undertaken by the intelligent agent on its environment is determined based on the one or more algorithms and data indicative of the past decisions of the person upon which the personal AI is based.

The present technique allows a first user (e.g. a surgeon) to seek advice from a personal AI of a second user (e.g. another surgeon) during a surgical procedure. In particular, the present technique allows the first user to access a plurality of personal AIs of a plurality of respective second users and, based on a number of factors, determine the most appropriate one or more of those personal AIs for use in providing AI generated information to assist the first user with the surgical procedure. In embodiments, the first user requests assistance from the personal AI of a second user by issuing an AI assistance request. This is in the form of a vocal command, for example. In response to this request, a suitable one or more personal AIs is chosen to generate information to assist the first user (this is referred to as AI assistance information). The generated AI assistance information is then returned to the first user. The AI assistance information may comprise any information usable by the first user to help them perform their role in the surgical procedure. For example, the AI assistance information may comprise one or more of information about the surgical procedure taking place, a recommended action to take or a recommended decision to make. In the case that the AI assistant comprises an intelligent agent, the AI assistant may act on the surgical environment (e.g. through actuating a surgical robot or the like) in addition to providing the AI assistance information.

FIG. 1 shows a surgical support system 100 according to an embodiment. The surgical support system 100 comprises one or more surgical data generating apparatuses (e.g. one or more of apparatuses 109 to 116) and a data processing apparatus 104.

The data processing apparatus 104 comprises a processor 105, memory 106, communication interface 107 and a storage medium 108. The communication interface 107 is for the input and output of electronic information to and from the data processing apparatus 104. For example, surgical data from the one or more surgical data generating apparatuses are received by the communication interface 107 as input information. The communication interface 107 also allows data to be exchanged between any two apparatuses connected to the communication interface 107. The processor 105 enables the data processing apparatus 104 to carry out its operations by processing suitable electronic instructions. The memory 106 is for storing electronic instructions to be processed by processor 105 and for storing input and output data associated with the electronic instructions. The storage medium 108 (e.g. in the form of a hard disk drive, solid state drive, tape drive or the like) is for long term storage of data. Each of the processor 105, memory 106, communication interface 107 and storage medium 108 are implemented using appropriate circuitry, for example.

The storage medium 108 stores each personal AI which may be consulted during the surgical procedure. It will be appreciated that, although the storage medium 108 is shown as part of the data processing apparatus 104, the storage medium 108 may be located on an external server (not shown) in communication with the data processing apparatus 104 via the communication interface 107. The external server is a cloud server, for example. Each personal AI comprises owner data and instructions for controlling the processor 105 to perform one or more algorithms using the owner data to generate AI assistance information. The owner data is data associated with the owner of the personal AI (that is, the user with respect to whom the personal AI is generated) that was recorded during one or more previous surgical procedures and which can be used (with the one or more algorithms) to predict a decision that the owner would make in a future surgical procedure. The AI assistance information is generated using the prediction made by the personal AI. For example, the AI assistance information comprises a predicted decision generated by the personal AI and recommends the predicted decision. More generally, the AI assistance information may comprise any information derivable from a prediction made by the personal AI concerned which is usable to help a user perform their role in the surgical procedure. In embodiments, AI assistance information is generated using a particular personal AI in response to receipt of an AI assistance request and selection of that personal AI (explained below) to provide the AI assistance information.

The communication interface 107 is operable to receive surgical data associated with the surgical procedure being performed by the surgeon. The surgical data is received from the one or more surgical data generating apparatuses during the surgical procedure. In the example of FIG. 1, there is a plurality of surgical data generating apparatuses which each provide surgical data to the communication interface 107.

Surgical data is data on the basis of which information about the surgical procedure currently taking place may be derived (this information comprising one or more surgical characteristics of the surgery, as will be explained). There is a plurality of types of surgical data. For example, the surgical data may be image data captured by one or cameras, location and/or motion data of a surgical robot and/or the surgeon (or other members of the surgical team) monitored by one or more sensors, physiological data of the patient and/or surgeon, audio data captured by one of more microphones or user data manually entered by a user using a suitable user interface. These example types of surgical data are non-exhaustive.

One example surgical data generating apparatus is a surgical robot 109. The surgical robot 109 is a robotic system which assists the surgeon in performing surgery. Various surgical robots are known in the art and surgery involving surgical robots is known as robot-assisted surgery. The surgical data provided to the communication interface 107 by the surgical robot 109 comprises, for example, values of one or more parameters associated with one or more functions of the robot carried out by the robot during the surgical procedure (e.g. the speed of a cutting blade used by the robot or the depth inside the patient of a robotic arm of the robot). The one or more parameters are monitored by appropriate circuitry of the robot, for example.

Another example surgical data generating apparatus is an external camera system 110. This comprises one or more cameras (not shown) which capture images of the operating room within which the surgery takes place. The captured images include, for example, the surgeon, the patient, other members of the surgical team and other surgical apparatuses in the room. The surgical data provided to the communication interface 107 by the external camera system 110 comprises the captured images.

Another example of a surgical data generating apparatus is an internal camera system 111. This comprises one or more cameras (not shown, e.g. one or more endoscopic cameras, as known in the art) which capture images inside the patient's body. The captured images may also include, for example, the surgeon's hands and any surgical apparatuses which enter the part of the patient's body captured by the internal camera system during the surgery (e.g. cutting tools held by the surgeon or an end of an arm of the surgical robot 109). The surgical data provided to the communication interface 107 by the internal camera system 111 comprises the captured images.

Another example of a surgical data generating apparatus is a patient monitoring system 112. The patient monitoring system monitors one or more physiological parameters of the patient during the surgery and generates data indicative of a value of each of these physiological parameters. This allows the status of the patient to be monitored during the surgery. An example of a patient monitoring system is an electrocardiograph (ECG) which generates ECG data. The surgical data provided to the communication interface 107 by the patient monitoring system 112 comprises the data indicative of the value of each of the monitored physiological parameters of the patient.

Another example of a surgical data generating apparatus is an audio monitoring system 113. This comprises one or more microphones (not shown) which capture sound in the operating room within which the surgery takes place. The captured sounds include, for example, speech uttered by the surgeon or other members of the surgical team and audible signals (e.g. alarms) emitted by other surgical apparatuses. The surgical data provided to the communication interface 107 by the audio monitoring system 113 comprises data indicative of the captured sounds. The data processing apparatus 104 is configured to analyse the captured sounds in order to determine what the captured sounds are. It does this, for example, by performing a frequency analysis of a captured sound and comparing the resulting frequency spectrum with the frequency spectrum of known sounds stored in the storage medium 108 (suitable techniques for this are known in the art). This allows the data processing apparatus 104 to, for example, recognise speech of the surgeon (allowing the surgeon to provide surgical data to the system vocally) or to recognise the meaning of specific audible signals emitted by other surgical apparatuses. In an embodiment, requests for AI assistance (including "expertise data" indicating the area of expertise for the AI assistance is required) is provided as a verbal command uttered by the surgeon which is recognised by speech recognition executed by the data processing apparatus 104.

Another example of a surgical data generating apparatus is a surgeon monitoring system 112. The surgeon monitoring system monitors one or more physiological parameters of the surgeon during the surgery and generates data indicative of a value of each of these physiological parameters. The surgeon monitoring system comprises, for example, a heart rate monitor to monitor the heart rate of the surgeon and/or a sweat monitor to monitor how much a surgeon is sweating (perspiring). This helps allow the stress levels of the surgeon to be monitored. For example, when the surgeon is more stressed, their heart rate tends to increase and they tend to sweat more and when the surgeon is less stressed, their heart rate tends to decrease and they tend to sweat less. The surgical data provided to the communication interface 107 by the surgeon monitoring system 114 comprises the data indicative of the value of each of the monitored physiological parameters of the surgeon.

Another example of a surgical data generating apparatus is a user interface 115. The user interface allows a user (e.g. the surgeon or another member of the surgical team) to manually enter surgical data to be provided to the communication interface 107. It also allows data output by the communication interface 107 (e.g. AI assistance information provided in response to a request for AI assistance) to be provided to the user in an understandable format. In one example, the user interface 115 comprises a touch screen or the combination of a head mountable display (HMD) and input device (e.g. handheld controller or keyboard). The user interface 115 may also comprise an audio loudspeaker. In one example, the surgical data entered by the user is data indicative of the type of surgical procedure to take place. Prior to the start of the surgical procedure, the user selects the surgical procedure type using, for example, an appropriate graphical user interface (GUI) menu system displayed on the touch screen or HMD. In another example, data output by the communication interface 107 comprises AI assistance information provided in response to a request for AI assistance. In response to receiving the AI assistance information, the touch screen or HMD outputs the AI assistance information in a visual form (e.g. in the form of text and/or an image) and/or the loudspeaker (if present) outputs the AI assistance information in an audible form (e.g. in the form of speech generated from text-to-speech processing of received textual AI assistance information or, in the case of the received AI assistance information comprising an audio file, by playing back the audio file). The user is thus able to interpret the received AI assistance information in a visual and/or audio form. In one example, when a HMD is used, the HMD may be an augmented reality (AR) HMD which allows a wearer to simultaneously view electronically generated images and a view of the real world (such HMDs include the Microsoft HoloLens (registered trademark), for example). The electronically generated images overlay (at an opaque or translucent manner, for example) the real world view of the user. The use of such AR HMDs allows AI assistance information to be provided to the user in a visual format whilst reducing any restriction of the user's real world field of view.

It will be appreciated that the user interface 115 may only be configured to allow AI assistance information to be provided by the data processing apparatus 104 to the user (rather than also being configured to allow surgical data to be provided by the user to the data processing apparatus 104). In this case, the user interface 115 is not a surgical data generating apparatus and the surgical data received by the communication interface 107 is received from one or more other surgical data generating apparatuses. In this case, the user interface 115 comprises one or more devices (e.g. an electronic display and/or loudspeaker) for providing the AI assistance information to the user.

Another example of a surgical data generating apparatus is a surgical navigation system 116. The surgical navigation system 116 helps determine the spatial location of various types of objects in the operating theatre. It may also help determine the spatial relationship between different objects. The objects include, for example, the anatomical target of the surgery and a tool used by the surgeon during the surgery. The surgical navigation system 116, once the respective locations of the anatomical target and tool have been detected, allows the spatial relationship between the anatomical target and the tool to be determine. This allows a suitable route to the anatomical target to the tool be determined, for example. The surgical navigation system 116 uses any suitable technique(s), such as stereoscopic imaging, computed tomography (CT) imaging or magnetic resonance imaging (MRI) in order to determine the spatial location of objects of interest in the operating theatre and, where appropriate, their spatial relationship to each other. A further discussion of surgical navigation techniques may be found in NPL 1, for example. The surgical data provided to the communication interface 107 by the surgical navigation system 116 comprises data indicative of the spatial location of each object of interest (e.g. in the form of coordinates in predetermined 3D coordinate system defined within the operating theatre). It may also comprise data indicating the spatial relationship between two or more of the objects of interest (e.g. in the form of a vector pointing from one object to another defined in the predetermined 3D coordinate system).

In the examples given here, the AI assistance request is made vocally (via the audio monitoring system 113 and speech recognition implemented by the data processing apparatus 104, for example). However, it will be appreciated that the AI assistance request may be made in any suitable way. For example, the user enter the AI assistance request via the user interface 115 (e.g. by typing the AI assistance request using a keyboard or selecting the AI assistance request from a GUI menu system).

Each surgical data generating apparatus which provides surgical data to the communication interface 107 does so via a suitable wired and/or wireless connection (as known in the art). The wired and/or wireless connection may be part of a computer network such as the internet.

In an embodiment, the surgical data is indicative of at least one of a type of the surgical procedure taking place and a current stage of the surgical procedure. The type of surgical procedure identifies which surgical procedure is performed by the surgeon. For example, the surgical procedure type may be a heart transplant, coronary artery bypass grafting or a knee replacement. As well as the surgical type, the operative method used for the surgery (e.g. if one type of surgery may be carried out using a plurality of different methods) may be determined. For example, if surgery type X can be carried out using a key hole method or a conventional method, then the specific method used (i.e. key hole or convention) will be determined. The current stage of the surgical procedure is one of a plurality of stages of the surgical procedure. Each stage is a sub-procedure of the surgical procedure. The stages of the surgical procedure must each be completed successfully in an appropriate order to allow the surgical procedure to be completed successfully. The necessary stages (and their order) will generally vary for different surgical procedure types. Examples of stages include making an incision on a certain organ of the patient, moving or removing a part of an organ of the patient and suturing an incision on a certain organ of the patient. The AI assistance information which is most useful to the surgeon at any given time will depend, in many instances, on the type of surgical procedure and the current stage of the surgical procedure.

FIGS. 2A-2C show example data stored in the storage medium 108 in the case of a first embodiment. In the first embodiment, a personal AI is selected based on the type and stage of the current surgical procedure, the desired expertise data included in the AI request and a number of scores associated with each selectable personal AI.

In this example, the surgical procedure is a heart transplant which has three stages. It will be appreciated that, in reality, a procedure such as a heart transplant is likely to contain a larger number of more complex stages. However, for the sake of clarity of explanation, only three stages of the procedure are shown here.

FIG. 2A shows the relationship between the procedure type and stage (in this case, the procedure type is "heart transplant" and the procedure stage is one of "stage one", "stage two" and "stage three"), the expertise data which may be sought during that stage and a plurality of personals AIs, each of which may provide a suitable response to a request indicating the expertise data.

It is noted that the personal AI data of each surgeon is stored in the storage medium 108. The relationship between the procedure type/stage, expertise data and personal AIs selected as candidates for providing a suitable response to a request indicating a given type of expertise data (as exemplified in FIG. 2A) is determined by the processor 105 using the personal AI data of each surgeon.

Thus, for example, during stage one of the heart transplant (which relates to the surgeon manually making an incision in the flesh between a heart and a lung of the patient), the surgeon may seek advice regarding the incision technique to use or the length of the incision which is to be made. In the case that the surgeon seeks advice on the incision device, they may provide a verbal command including the words "incision technique".

For example, the surgeon may say the phrase "AI assistant: tell me information about the incision technique to use". In response to this command, the data processing apparatus 104 looks up unique identifiers (AI IDs) of personal AIs which are known to be able to provide information on the incision technique to use during stage one of the heart transplant. In this case, personal AIs with a AI ID "AI 1", "AI 2" and "AI 3" are associated with the expertise data "incision technique" for stage one of a heart transplant.

In another example, the surgeon seeks information on the incision length of the incision to be made in stage one of the heart transplant. In this case, the surgeon issues a command asking for information about the incision length (for example, the surgeon may say "AI assistant: tell me information about the incision length"). In this case, the data processing apparatus 104 looks up the AI IDs associated with the "incision length" expertise data in the table of FIG. 2A. In this example, the AI IDs associated with "incision length" are the same as those associated with "incision technique" (namely, AI 1, AI 2 and AI 3).

A similar situation applies for expertise data sort during other stages of the heart transplant.

In particular, during stage two of the heart transplant (which involves attaching a blood vessel to the transplanted heart), the expertise that may be sought by the surgeon includes "attachment equipment" (relating to the most appropriate equipment to use in attaching the blood vessel to the transplanted heart), "damage avoidance" (relating to the most appropriate action to avoid damage to the transplanted heart) and "attachment success" (relating to the best way to test whether the blood vessel has been successfully attached to the heart prior to the surgeon moving onto the next stage of the procedure). These types of expertise data are associated with different sets of AI IDs. In particular, "attachment equipment" is associated with AI 3, AI 5 and AI 6, "damage avoidance" is associated with AI 5, AI 6 and AI 7 and "attachment success" is associated with AI 3, AI 5 and AI 6.

Stage three of the heart transplant (which relates to making an incision using a surgical robot) is associated with a single piece of expertise data called "incision planning". This relates to how best to plan the incision to be made using the surgical robot. The AI IDs associated with "incision planning" are AI 1, AI 7 and AI 8. Thus, depending on the procedure type and stage and on the expertise data indicated in the request from the surgeon, the data processing apparatus 104 looks up the AI IDs associated with that procedure type/stage and expertise data in the table of FIG. 2A.

Each of the AI IDs relates to a previously configured personal AI. A personal AI is a set of data associated with a person and represents the decisions made in relation to one or more predetermined areas of expertise (e.g. incision technique during stage 1 or a heart transplant, attachment success during stage 2 of a heart transplant, etc.) during a previous instance of the surgical procedure. Each personal AI may be a machine learned data set, for example, in which information associated with the expertise area is collected during previous surgical procedures and classified according to the success (or not) of that stage of the procedure.

Thus, for example, AI 1 may be the personal AI of a surgeon with a particularly high success rate for making the manual incision required in stage 1 of the heart transplant. AI 1 is therefore considered an appropriate AI to consult if the surgeon carrying out the current heart transplant requires advice on the incision technique or incision length required during stage 1 of the current heart transplant.

Similarly, for example, AI 3 may be the personal AI of a surgeon with a typically high success rate for the attachment of a blood vessel to a transplanted heart. In the example of FIG. 2A, this surgeon is known to have particular expertise in the areas of which equipment to use and in assessing the success of a blood vessel attachment. AI 3 therefore appears in the table of FIG. 2A for the expertise data "attachment equipment" and "attachment success" for stage 2 of the heart transplant. In this particular case, however, the surgeon associated with AI 3 is not considered to be an expert in relation to avoidance of damage to the transplanted heart during the blood vessel attachment (e.g. the surgeon associated with AI 3 may not have a sufficient success rate in avoiding damage to the transplanted heart during blood vessel attachment). AI 3 therefore does appear as an AI ID associated with the "damage avoidance" expertise data for stage two of the heart transplant. Instead, AI 7 (the personal AI of another surgeon) is included as an AI ID in the table of FIG. 2A for the expertise data "damage avoidance" (together with AI 5 and AI 6 which are also present for the "attachment equipment" and "attachment success" expertise data).

It is noted that each area of expertise of a particular personal AI is associated with a respective instance of expertise data in FIG. 2A. The term "expertise data" should be understood to mean the information included in the request from the surgeon. The expertise data uniquely identifies the area of expertise of which the surgeon is requesting information. For example, "incision technique" (during stage 1 of the heart transplant) is the expertise data associated with the area of expertise of what is the most appropriate incision technique to use. Similarly, "attachment equipment" (during stage 2 of the heart transplant) is the expertise data associated with the area of expertise of what is the most appropriate equipment to use to attach the blood vessel to the heart. Each AI ID listed in the table of FIG. 2A for a particular instance of "expertise data" is thus also associated with the area of expertise indicated by that expertise data.

The storage medium 108 may contain a large number of personal AIs (each with a unique AI ID). The selection of which AI IDs in the table of FIG. 2A are associated with particular expertise data is determined based on a suitable parameter in each personal AI indicating the competence of the surgeon associated with that personal AI for that particular area of expertise during the surgical type/stage concerned. The competence may be determined by looking for a relationship between a surgeon's success rate of a particular surgical type/stage and one or more predetermined features of the surgeon's work (e.g. techniques or tools used) in completing that particular surgical type/stage.

For example, the surgeons associated with each of AI 1, AI 2, and AI 3 all have a sufficiently high success rate for stage 1 of the heart transplant for both the "incision technique" and "incision length" expertise data. This indicates a consistency between the incision technique used by each of these surgeons and the successful outcome of stage 1 of the heart transplant and also a consistency in the incision length used by each of the surgeons and the successful outcome of stage 1 of the heart transplant. This allows the success of a particular stage of the procedure to be associated with the incision technique and incision length used.

On the other hand, during stage 2 of the procedure, although the surgeon associated with AI 3 has a successful track record with this procedure (hence AI 3 is included in two of the three expertise categories in FIG. 2A for stage 2), AI 3 does not appear for the "damage avoidance" expertise data. This is not necessarily because the damage avoidance techniques employed by the surgeon associated with AI 3 were not successful. Rather, it may be because different successful stage 2 procedures have been carried out by the surgeon associated with AI 3 using a range of different damage avoidance techniques. There is thus no particular relationship between the damage avoidance technique used by the surgeon associated with AI 3 and their high success rate in completing stage 2. The benefit of seeking advice from the surgeon associated with AI 3 for seeking an appropriate damage avoidance technique is therefore limited (since the particular damage avoidance technique used by this surgeon does not appear to relate to the success rate of the surgeon).

The AI IDs associated with each type of expertise data for each procedure type/stage may be determined according to any other suitable parameter derivable from the personal AI associated with each AI ID. The above example uses the success rate for the particular type/stage of the procedure concerned. For example, all AI IDs of surgeons with a success rate greater than a predetermined success rate may be included in the table of FIG. 2A (with the specific type(s) of expertise data with which each AI ID is associated depending on the parameter(s) derivable from the personal AI concerned, as discussed). It will be appreciated, however, that another metric of success which is derivable from the data making up the personal AI could be used. For example, all personal AIs which reflect a certain level of experience (e.g. those which have completed more than a predetermined number of instances of the procedure concerned) in the surgical type/stage concerned may be included in the table of FIG. 2A (again, with the specific type(s) of expertise data with which each AI ID is associated depending on the parameter(s) derivable from the personal AI concerned, as discussed). The filtering of the most appropriate personal AI to consult is then carried out in the subsequent steps (to be explained).

It is noted that an area of expertise may be relevant to a particular type of surgical procedure (e.g. heart transplant) as a whole. Alternatively, an area of expertise may be relevant only to a particular stage of that type of surgical procedure (e.g. stage 1 of the heart transplant). It is therefore said that each area of expertise (and hence each type of expertise data) is associated with a particular procedure type/stage (that is, a particular type of surgical procedure overall or a particular stage of a particular type of surgical procedure).

As previously mentioned, in an example, the surgeon may select the type of surgical procedure (e.g. "heart transplant") which is to take place prior to the start of the surgical procedure using a suitable GUI menu system or the like. During the surgical procedure, the data processing apparatus 104 may be configured to detect the current stage (e.g. "Stage 1", "Stage 2" or "Stage 3") of the surgical procedure (enabling it to look up the appropriate potential error event(s) and associated acceptable error likelihood(s) and intervention type(s) for that stage) in one or more various ways.

In one example, a user (e.g. the surgeon or another member of the surgical team) may manually update the system each time the procedure moves on to a new stage. This may be done, for example, via the user interface 115 (e.g. by selecting the current stage from a list of the stages of the current procedure shown on a GUI menu system or the like) or via the audio monitoring system 114 (e.g. by saying a predetermined command, such as one or more words which uniquely identify the desired stage of the procedure, which is picked up by the audio monitoring system 113 and which is recognisable by the data processing device 104).

In another example, the data processing device 104 is configured to automatically detect the current stage of the procedure. In one example, this is done using a suitable machine vision image comparison technique (such methods are known in the art and will therefore not be discussed in detail here). At regular intervals during the procedure, an image is captured by the external and/or internal camera system 110, 111 and one or more image characteristics of the captured image are compared with a corresponding one or more characteristics of each of images of a previous instance of the surgical procedure. Each image of a previous instance of the surgical procedure is an image known to have been captured at a particular stage of that previous instance of the surgical procedure. The particular stage of an image of a previous instance of the surgical procedure with the closest match with the captured image is determined to be the current stage of the procedure. In an example, the one or more characteristics of the captured image and each of the images of a previous instance of the procedure which are compared are determined using a machine learning classification technique. That is, each image of a previous instance of the procedure is manually classified as belonging to a particular stage of the procedure and a machine learning algorithm automatically determines one or more characteristics which distinguish that image from images belonging to other stages of the procedure. Those one or more characteristics are then analysed in a newly captured image (for which the classification is unknown) in order to determine the likely classification of that newly captured image.

Thus, for example, for the heart transplant surgical procedure of FIG. 2, at least one image for each of Stage 1, Stage 2 and Stage 3 will have been captured and manually classified as "Stage 1", "Stage 2" or "Stage 3" by a human user for one or more previous instances of a heart transplant procedure. The machine learning algorithm will have automatically determined one or more characteristics of each of these images which are indicative of the particular stage with which that image is associated. That is, the machine learning algorithm, given the images and manually applied classifications, will automatically determine one or more characteristics which distinguish a "Stage 1" image from a "Stage 2" or "Stage 3" image, one or more characteristics which distinguish a "Stage 2" image from a "Stage 1" or "Stage 3" image and one or more characteristics which distinguish a "Stage 3" image from a "Stage 1" or "Stage 2" image. During the procedure of FIG. 2, each image captured by the external or internal camera system 110, 111 is analysed in order to determine, based on the one or more characteristics of the previously captured "Stage 1", "Stage 2" and "Stage 3" images, whether or not the image is most likely to be "Stage 1", "Stage 2" or "Stage 3". The stage with which the image is most likely to be associated is then determined to be the current stage of the procedure.

Various machine learning algorithms are known in the art and will therefore not be discussed in detail here. It will be appreciated that the greater the number of images of the various stages of previous instances of the procedure and the greater the number of previous instances of the procedure from which those images are generated, the more reliable the determination of the current stage of the current procedure. Previous images may also be captured, for example, from different angles and/or under different lighting conditions in order to help provide more reliable determination of the current stage of the procedure (since the angle of view and/or lighting conditions for captured images of the current procedure are likely to vary for different instances of the procedure). Data indicative of the one or more characteristics of images of previous instances of the procedure for analysis of newly captured images of the current procedure is stored in the storage medium 108, for example.

In an embodiment, the automatic determination of the current stage of the surgical procedure may be confirmed manually by the surgeon (or another member of the surgical team) during the procedure. This helps to alleviate the risk of surgical errors taking place due to an erroneous determination of the current stage of the procedure (e.g. erroneous determination of "Stage 3" when it is actually "Stage 2" being carried out, meaning that inappropriate AI assistance information could be given to the surgeon). In one example, this manual confirmation comprises inputting a confirmation command via the user interface 115 and/or audio monitoring system 112. For example, the user interface 115 displays the message "Automatic procedure stage detection=X—press OK or say CONFIRM to confirm" (wherein X is the name of the stage, e.g. "Stage 1", "Stage 2" or "Stage 3" for the example procedure of FIG. 2). If the user presses "OK" (e.g. "OK" being a virtual button displayed on a touch screen of the user interface 115) or vocally says "Confirm" (this being picked up by the audio monitoring system 113), then the data processing apparatus 104 knows that it has correctly determined the current surgical stage. On the other hand, if the user does not carry out this confirmation action within a predetermined time limit (e.g. 5 or 10 seconds), then the data processing apparatus 104 does not rely on the automatically determined current stage of the procedure and, instead, awaits further input from the user in order for the current stage of the procedure to be manually selected.

The concept of automatically determining the current stage of the procedure based on a comparison between one of more characteristics of a newly captured image of the current procedure and one or more corresponding characteristics of one or more images of a previous instance of the procedure may be applied to the other types of surgical data which can be collected during the current and previous instances of the surgical procedure. For example, this may be applied to (i) surgical data generated by the surgical robot, (ii) surgical data generated by the patient monitoring system, (iii) audio data collected by the audio monitoring system 113 during the current and previous instances of the surgical procedure (including verbal communication between members of the surgical team, audible machine alarms and the like) and/or (iv) surgical data generated by the surgeon monitoring system 114.

Different types of surgical data may be used to independently confirm the occurrence of particular events during the surgical procedure which are indicative of a particular stage of the surgical procedure taking place. In one example, the tools used by the surgeon at any given time during the procedure may be detected using both image recognition in images captured by the external and/or internal camera systems 110, 110 and monitoring devices on the tools (e.g. accelerometers forming part of the surgeon monitoring system 114) which output a signal as surgical data to the communication interface 107 when the tool concerned is picked up as opposed to being stationary on a surface. The use of a particular combination of tools may be mapped (in a database stored in storage medium 108, for example) to a particular stage of the procedure, thereby allowing the occurrence of that stage to be detected.

A problem with personal AIs of the type described is that the preferences of each surgeon with regard to techniques, tools and the like differ and therefore, for example, even if a particular personal AI which may be consulted has a high success rate for a particular procedure type/stage, the advice provided by that personal AI may not be appropriate to the surgeon carrying out the current procedure (e.g. it may suggest use of a tool or technique that the surgeon does not like or is not competent with).

Another problem is that the particular surgeon associated with a personal AI may not update the AI sufficiently frequently. Thus, for example, if a particular personal AI is associated with a high success rate (and is therefore included in the table of FIG. 2A) but has not been updated by the surgeon sufficiently recently in order to take into account more recent medical developments, then the techniques (for example) recommended by the personal AI may not be the most up to date available.

Another problem occurs if the personal AI does not contain enough data. For example, if a surgeon has successfully completed only a small number of procedures (for example, only one or two), then this is not a statistically significant number of successes to enable the conclusion that the techniques of the surgeon contributed to their success (for example, it may just have been luck).

In addition, a particular surgeon may have admiration or respect for a particular colleague and may wish for that colleague's personal AI to be given preference over that of a stranger.

Such problems may slow the uptake in use of surgical AI assistants.

In order to alleviate this problem, each AI may be associated with one or more scores which indicate certain AI characteristics of that AI. These scores may then be used in order to determine the personal AI (or personal AIs) which are used to respond to a surgeon's request.

FIG. 2B shows an example of such a score. This is a "requester relationship" score. In this case, the AIs concerned are AI 3, AI 5 and AI 6. According to the table of FIG. 2A, these are candidates to provide AI assistance to the surgeon for requests seeking advice on the "attachment equipment" and "attachment success" areas of expertise during stage 2 of the heart transplant. However, it will be appreciated that this principle may be applied to the group of personal AIs associated with any areas of expertise of a given procedure type/stage). The data representing the table of FIG. 2B is stored in the storage medium 108, for example.

FIG. 2B shows a requester relationship score for each of the personal AIs. This is a score which indicates the quality of the relationship (i.e. the level of trust) between the surgeon carrying out the current procedure (the requester, as indicated by the surgeon providing suitable identity credentials via the user interface 115, for example) and the surgeon associated with each of the personal AIs AI 3, AI 5 and AI 6. The score may take any value from 1 to 10, with a higher number indicating a stronger relationship and a lower number indicating a weaker relationship. It can be seen that the surgeon has the best relationship with the surgeon associated with the personal AI 6 (with a requester relationship score of 9). The surgeon associated with AI 6 may be a respected colleague of the surgeon carrying out the procedure, for example. The next strongest relationship is that between the surgeon carrying out the current procedure and the surgeon associated with AI 5 (with a requester relationship score of 8). This may be a close friend of the surgeon, for example. The weakest relationship is that between the surgeon carrying out the current procedure and the surgeon associated with AI 3 (with a requester relationship score of 2). In this case, the surgeon of AI 3 may be an unknown doctor to the surgeon currently carrying out the procedure.

The requester relationship score for a particular surgeon may be determined by any suitable method. For example, each surgeon who engages with the present technique may have a professional social media profile on a professional social media network which is linked to their personal AI identifier (AI ID). Depending on the amount of interactivity between the surgeon currently carrying out the procedure and each other surgeon with which they are connected (or not), the surgeon relationship score may be determined.

In one example, it is seen from the professional social media profiles of the current surgeon and the surgeon of AI 6 that they have worked together at the same hospital for a long time, have attended similar training courses and have conducted many surgical procedures together. It is therefore determined that the surgeon of AI 6 is a respected colleague of the current surgeon. A requestor relationship score of 9 is therefore allocated to the surgeon of AI 6.

In another example, it is derivable from the professional social media network that the current surgeon and the surgeon of AI 5 have a lot of interaction via the professional social media network. For example, they may share photos, messages and professional articles or the like on a regular basis. The current surgeon and the surgeon of AI 5 do not work together, however (rather, they work at different hospitals but may have attended medical school together, for example). In this case, the system determines that the current surgeon and the surgeon of AI 5 are close friends and therefore provides a requester relationship score of 8.

In another example, the current surgeon and the surgeon of AI 3, although both part of the professional social media network, are not linked on the professional social media network (e.g. they are not registered as "colleagues" or "friends") and have never exchanged any information using the professional social media network. The system therefore concludes that the current surgeon and a surgeon of AI 3 do not know each other and thus assigns a low requester relationship score of 2.

In an embodiment, the professional social media data of each surgeon is stored on a network server (not shown) in communication with the communication interface 107 of the data processing apparatus 104. This allows the data processing apparatus 104 to receive the professional social media data from each surgeon and to thereby generate the requestor relationship scores between the current surgeon and the surgeon of each personal AI identified as a candidate for providing a response to a request from the current surgeon.

The relationship between different surgeons may be analysed in any other suitable way. For example, surgeons with a personal AI may be able to mutually agree a requester relationship score between them (e.g. the current surgeon suggests a relationship score of 8 to the surgeon of AI 5 and this relationship score is confirmed if the surgeon of AI 5 agrees with this suggested score of 8). The relationship score of two surgeons is thus agreed by mutual consensus.

FIG. 2C shows two other example types of scores with which each of the personal IDs is associated.

The first score is an "advice value" score indicating the competence of the personal AI to provide advice relating to the expertise data concerned. The advice value score is generated based on the personal AI data itself, for example. In an embodiment the advice value score is used in order to determine which of the personal AIs are associated with each type of expertise data for a given procedure type/stage (as exemplified in FIG. 2A). Each advice value score therefore indicates, for example, the competence of the surgeon to whom the personal AI belongs for the procedure type/stage and type of expertise data concerned (as previously discussed). For example, a particular personal AI may only be entered as a candidate for a given type of expertise data for a particular procedure type/stage if the advice value score is greater than or equal to a predetermined threshold advice value score (e.g. 5 or more if the advice value score is determined to be between 1 and 10).

The second score is a "training quality" score. This is a score which indicates the amount of interaction between each surgeon and their personal AI in order to keep the personal AI up to date and/or to provide the personal AI with sufficient data so as to enable it to provide reliable advice. The training quality score for each personal AI may be calculated according to any suitable technique. For example, the training quality score may be calculated based on the amount of data contained in the surgeon's personal AI (with more data providing a higher training quality score and less data providing a lower training quality score) and/or how often the surgeon engages with their personal AI in order to keep it up to date (with a higher training quality score for a more frequently updated personal AI and lower training quality score for a less frequently updated personal AI).

In the example of FIG. 2C, AI 3 has a advice score of 7 and an engagement score of 10. AI 5 has an advice score of 7 and an engagement score of 5 (indicating that, although AI 3 and AI 5 have a similar success rate, the surgeon of AI 3 engages with their personal AI by building the data contained in their personal AI and/or updating it more frequently than the surgeon of AI 5). AI 6 has a lower advice value score of 5. However, their engagement score is high at 9, therefore implying that the advice value score is based on more and/or more up to date data and therefore has high reliability.

The requester relationship score between each pair of surgeons, the advice value score of each surgeon's personal AI and the training quality score of each surgeon's personal AI is stored in the storage medium 108.

In an embodiment, each personal AI will have a separate advice value score for each type of expertise data and procedure type/stage combination. For example, in FIG. 2C, the advice value scores for AI 3 (as well as for AI 5 and AI 6) are for the 'attachment equipment' expertise data of stage 2 of the heart transplant. AI 3 will have a separate advice value score for the "attachment success" expertise data of stage 2 of the heart transplant, for the "damage avoidance" expertise data of stage 2 of the heart transplant, for the "incision technique" expertise data of stage 1 of the heart transplant, etc. It is noted that, although AI 3 does not appear for the "damage avoidance" expertise data of stage 2 of the heart transplant in FIG. 2A, AI 3 will still have an advice value score defined for this type of expertise data and procedure type/stage combination. However, this advice value score is too low (i.e. less than the predetermined threshold advice value score) for AI 3 to be listed as a candidate personal AI for the "damage avoidance" expertise data of stage 2 of the heart transplant.

In an embodiment, the requester relationship score and training quality score of each personal AI is the same for each type of expertise data and procedure type/stage combination. However, it will be appreciated that, in another embodiment, the request relationship score and training quality score of each personal AI could differ depending on the type of expertise data and procedure type/stage combination.

FIG. 3 demonstrates the aggregation of the scores associated with each candidate AI which is to respond to the surgeon's request, according to an embodiment. As discussed with reference to FIGS. 2B and 2C, AI 3 (belonging to an unknown doctor) has a requester relationship score of 2, an advice value score of 7 and a training quality score of 10. This provides an aggregate score of 2+7+10=19. A 15 (belonging to the surgeon's close friend) has a requester relationship score of 8, an advice value score of 7 and a training quality score of 5. This provides an aggregate score of 8+7+5=20. AI 6 (belonging to the respected colleague of the surgeon) has a requester relationship score of 9, an advice value score of 5 and a training quality score of 9. This provides an aggregate score of 9+5+9=23. The most appropriate personal AI to answer the surgeon's request is therefore AI 6 (with the highest aggregate score), followed by AI 5 (with the next highest aggregate score), followed by AI 3 (with the lowest aggregate score).

In this case, the data processing apparatus 104 is configured to provide three instances of assistance information in response to the surgeon's request.

One of these instances of information is general AI advice. This is predetermined advice which is associated with the procedure type/stage and expertise data identified in the surgeon's request. The general AI advice is related to the procedure type/stage and expertise data in a database like that shown in FIG. 2A (the difference being that the column 'AI ID' is replaced with a column having rows which indicate the location of information representative of the relevant general AI advice stored in the storage medium 108, for example). The general AI advice is not associated with any particular personal AI of a real life surgeon. Rather, it is preconfigured information (from a surgical textbook or the like) relevant to the current procedure type/stage and expertise data for which advice is sought.

The general AI advice may include, for example, success rate information associated with the current procedure type/stage and expertise data (e.g. for stage 1 of a heart transplant and "incision technique" expertise data, a historical success rate associated with one or more respective types of incision technique), patient quality of life (QOL) information associated with the current procedure type/stage and expertise data (e.g. for stage 1 of a heart transplant and "incision technique" expertise data, a numerical indicator based on historical data and indicative of a level of post-surgery patient comfort or discomfort associated with one or more respective types of incision technique) or surgical efficiency information (e.g. for stage 1 of a heart transplant and "incision technique" expertise data, an estimated completion time associated with one or more respective types of incision technique). It will be appreciated that the general AI advice may be provided concurrently with the personal AI advice. Furthermore, the general AI advice may be selected depending on the recommendation of the personal AI(s) used to generate the personal AI advice. For example, if AI 1 is selected as a personal AI for stage 1 of a heart transplant and "incision technique" expertise data, then the general AI advice may provide information associated specifically with the incision technique(s) recommended by AI 1.

The further two instances of information are opinions provided by the personal AIs AI5 and AI6, respectively. These AIs have been selected because they have the highest and next highest aggregate scores.

Thus, with the present technique, the AI assistance information provided to the current surgeon from one or more personal AIs of one or more other surgeons is selected using a plurality of different scores, each score being indicative of a respective AI characteristic of that personal AI (e.g. the characteristics of advice value, requester relationship and training quality). The AI assistance information provided to the surgeon is therefore more appropriately tailored to the surgeon's needs, thereby allowing relevant AI assistance information to be provided to the surgeon more easily and efficiently.

FIGS. 4A and 4B show another embodiment of the present technique.

FIG. 4A shows another example of a table relating various procedure type/stages, expertise data and AI ID. The table of FIG. 4A is the same as the table of FIG. 2A, except that it has an additional column titled 'relevant team members'. For each procedure type/stage and expertise data type combination, the 'relevant team members' column indicates the members of the surgical team whose preferences will be taken into account in selecting the personal AI which is to provide a response to an issued request for AI assistance information. In an example, prior to the beginning of the surgical procedure, each team member who will take part in the procedure is identified. The preferred AI ID associated with each identified team member is also identified prior to the beginning of the surgical procedure (as are any other further preferences of that team member). An example of the identified team members' preferred AI IDs and other preferences for the 'attachment equipment' expertise data of stage two of the heart transplant are shown in FIG. 4B. The data indicating the relevant team members for each procedure type/stage and expertise data combination (as exemplified in FIG. 4A) and the data indicating the preferred AI ID and any further preferences of each team member (as exemplified in FIG. 4B) are stored in the storage medium 108.

In an example, prior to the beginning of the surgical procedure, a member of the surgical team will identify each team member by entering information using the user interface 115 (e.g. using touch screen keyboard or graphical user interface (GUI) interactive menu system of a touch screen of the user interface 115). Each team member is identified using a unique member ID which uniquely identifies that member. In this case, the surgical team has three members whose preferences may affect the selected personal AI used to provide AI assistance. These are the surgeon (with unique member ID 'Member 1'), a camera operator (with unique member ID 'Member 2') and a nurse (with unique member ID 'Member 3'). The preferred AI ID of the candidate AI IDs identified in FIG. 4A for the expertise data "attachment equipment" for stage 2 of the heart transplant is AI 3 for Member 1. For Member 2, the preferred AI ID is AI 5. For Member 3, the preferred AI ID is AI 3. In addition, Member 1 has a further preference indicating a monitor visualisation style (i.e. that monitor visualisation style 'x' is selected). This relates to the way in which an image appears on a display (monitor) of the user interface 115 during the surgical procedure (e.g. specifying any effects to be applied to the image which make it easier for Member 1 to understand what is going on). Similarly, Member 2 has a preference for any alerts issued by surgical apparatuses during the surgical procedure to be audible alerts only (e.g. other types of alerts, such as visual and/or haptic alerts are disabled). Member 3 does not have any further preferences.

In an embodiment, the preferred AI ID and other preferences of each of Members 1, 2 and 3 is defined separately for each procedure type/stage and expertise data combination for which that member is one of the relevant team members. The preferred AI ID(s) of each team member may be manually selected by that team member (e.g. via the user interface 115). Alternatively, the process of FIG. 3 may be carried out for each relevant member of the team in order to determine the candidate AI ID with the highest aggregate score for that team member. The AI ID with the highest aggregate score is then selected as the preferred AI ID for that team member. For example, the preferred AI IDs for each team member in FIG. 4B may result from Member 1 (the surgeon) having an aggregate score of 25 for AI 3, 18 for AI 5 and 19 for AI 6 (meaning that AI3, with the highest aggregate score of 25, is determined to be the preferred AI ID of the surgeon), Member 2 (the camera operator) having an aggregate score of 19 for AI 3, 20 for AI 5 and 15 for AI 6 (meaning that AI 5, with the highest aggregate score of 20, is determined to be the preferred AI ID of the camera operator) and Member 3 (the nurse) having an aggregate score of 22 for AI 3, 21 for AI 5 and 17 for AI 6 (meaning that AI 3, with the highest aggregate score of 22, is determined to be the preferred AI ID of the nurse).

In an example, during stage 2 of the heart transplant, the current surgeon asks for AI assistance relating to which attachment equipment to use (e.g. the surgeon issues the verbal request "AI assistant: tell me about which attachment equipment to use"). In response to this, the data processing apparatus 104, upon detecting the procedure type/stage from the surgical data and upon detecting the desired expertise data from the surgeon's verbal request, determines (from the table of FIG. 4A) that personal AIs AI 3, AI 5 and AI 6 are appropriate candidate personal AIs for providing the required AI assistance.

The data processing apparatus 104 then looks at the 'relevant team members' column of the table of FIG. 4A to determine the relevant team members associated with the expertise data "attachment equipment" for stage 2 of the heart transplant. The relevant team members for each procedure type/stage and expertise data combination are the members of the surgical team whose preferences are allowed to effect the candidate personal AI which is chosen to provide the AI assistance. In this case, the relevant members of the surgical team are the surgeon, the camera operator and the nurse. The preferences of each of these team members (each of the surgeon, the camera operator and the nurse having been previously identified prior to starting the surgery as, respectively, Member 1, Member 2 and Member 3) is therefore taken into account.

In an example, the personal AI is selected based on a majority vote. Thus, in this case, the preferred AI ID of the surgeon and of the nurse is AI 3 whereas the preferred AI ID of the camera operator is AI 5. The vote is therefore two votes for AI 3 to one vote for AI 5. AI3 is therefore selected. In the case of a tie (for example, if each of the surgeon, the camera operator and the nurse have a different respective AI ID as their preferred AI ID), then the preferred AI ID of a predetermined member of the team (e.g. the surgeon) is given priority and is selected. In any case, however, any other preferences (if present) of each of the team members are applied, if possible. In the case of a clash of preferences (e.g. if the surgeon wishes for a first visualisation style to be displayed on a monitor but the camera operator has a preference for a second, different visualisation style to be displayed on the same monitor) then, again, the preferences of a predetermined member of the team is given priority (e.g. the surgeon).

In an embodiment, a preferred AI ID may be defined for a team of people. For example, a preferred AI ID (for a given procedure type/stage and expertise data combination) may be defined for a team comprising a particular surgeon (e.g. "Member 1"), camera operator (e.g. Member 2") and nurse (e.g. "Member 3") who regularly work together and have a successful team chemistry. The AI ID associated with that team is stored in the storage medium 108. During a surgical procedure involving these three people, the AI ID which is indicated as being preferred by that team for the given procedure type/stage and expertise data combination concerned is selected. This helps provide the most appropriate personal AI for a team of people working together, thereby improving team performance.

In an embodiment, when there are multiple possible AI IDs associated with a particular surgery type/stage and expertise data combination, AI assistance information may be provided from each of those multiple personal AIs simultaneously. However, the way in which each instance of AI assistance information is provided may vary depending on the preferences of the team members or team as a whole. For example, for the "attachment equipment" expertise data for stage 2 of the heart transplant, AI assistance information may be provided from each of AI 3, AI 5 and AI 6. However, since the overall preference (based on a majority vote of each of "Member 1", "Member 2" and "Member 3") is for AI 3, the assistance information from AI 3 may be presented differently to the assistance information from AI 5 or AI 6. For example, if the assistance information of each of AI 3, AI 5 and AI 6 is provided in a visual format, the AI 3 assistance information may be presented in a larger and more central visual format than the AI 5 or AI 6 visual information. This allows all available AI assistance information to be provided (thereby providing the surgical team with all information which may help them) but also allows the preferred AI assistance information to be easily recognised by the surgical team. In an embodiment in which the AI assistance information is provided using an AR HMD, for example, the AI assistance information of the preferred AI (e.g. AI 3 in this case) may be provided centrally in the field of view of the user in a larger visual format whereas the other AI assistance information (e.g. AI 5 and AI 6 in this case) may be provided in the periphery of the field of view of the user in a smaller visual format. It will be appreciated that, as the procedure type/stage and/or sought expertise data changes, the AI assistance information displayed will change to reflect this (taking into account the personal AI preferences of each team member and/or the team overall).

Thus, with the present technique, the AI assistant is selected taking into account the preferences of each relevant member of the surgical team. The AI assistance information provided is therefore more appropriately tailored to the needs of the surgical team overall, thereby allowing relevant AI assistance information to be provided to the surgical team more easily and efficiently.

Figure 5:
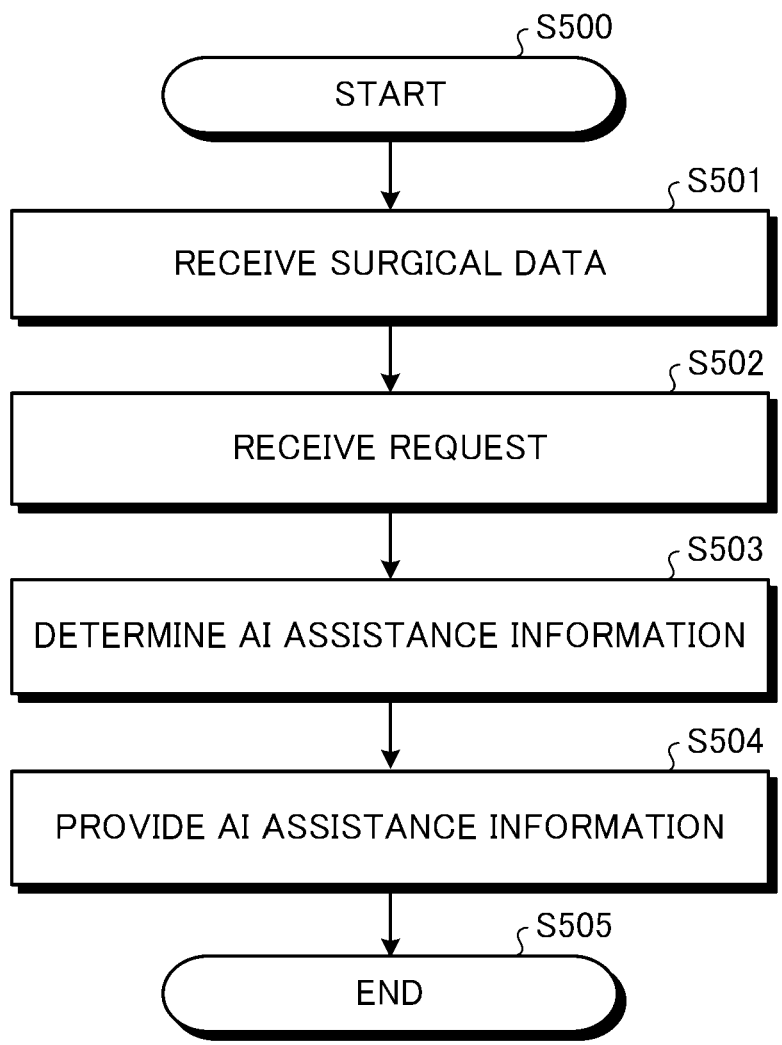
FIG. 5 shows a flow chart showing a method, according to an embodiment.

FIG. 5 shows a flow chart showing a method implemented by the data processing apparatus 104, according to an embodiment. The method starts at step 500. At step 501, the communication interface 107 receives surgical data generated by one or more of the surgical data generating apparatuses 109 to 116. At step 502, the communication interface 107 receives, from a user, a request for artificial intelligence (AI) assistance information. The request comprises a signal transmitted from the audio monitoring system 113 in response to the user uttering a verbal AI assistance information request, for example. Step 502 is optional, since the AI assistance information may be generated automatically (that is, without a request from the user) in response to receipt of the surgical data (see below). At step 503, the processor 105 determines the AI assistance information using the surgical data (e.g. as exemplified in FIGS. 2, 3 and/or 4). At step 504, the communication interface 107 provides the determined AI assistance information to the user (e.g. by sending a suitable signal to a display of the user interface 115 to display the determined AI assistance information). The process ends at step 505.

In an embodiment, a personal AI used in the present technique is implemented as a combination of computer software and a stored set of data. The computer software, when run on an appropriate device (e.g. the data processing apparatus 104), provides a virtual interface (e.g. via the user interface 115) via which information can be provided to and/or received from a participant of the surgical procedure (that is, a member or members of the surgical team carrying out the surgical procedure).

The stored set of data (e.g. stored in the storage medium 108) comprises characteristic data indicative of a characteristic of a previous surgical procedure (not to be confused with the above-mentioned AI characteristic) carried out by the person (e.g. surgeon) on whom the personal AI is based and decision data indicative of a decision made by that person which is associated with the characteristic data. The device on which the personal AI is run is also able to receive surgical data indicative of a characteristic of the current surgical procedure. The surgical data is generated by one or more devices used during the surgical procedure (e.g. devices 109 to 116) and received by the on which the personal AI is run. The characteristic data of the stored set of data is surgical data generated during the previous surgical procedure, for example. The decision data associated with the characteristic data is indicative of a decision made by the person on whom the personal AI is based at the time at which the characteristic data was generated. The decision data is recorded with its associated characteristic data in any suitable way (e.g. manually by someone entering information indicative of the decision made by the participant via a suitable user interface during the previous surgical procedure or automatically based on image recognition of images captured during the previous surgical procedure).

The computer software comprises one or more algorithms which are configured to compare the surgical data acquired during the current surgical procedure with the characteristic data of the stored set of data. Based on the comparison, information indicative of a decision made by the person on whom the personal AI is based is output to the participant. In one example, the output information is indicative of the decision associated with the characteristic data with the closest match to the received surgical data. In an embodiment, determination of an appropriate decision based on the received surgical data and the stored set of data is determined using an appropriate machine learning algorithm (such as a neural network or the like). Various machine learning algorithms are known in the art and are therefore not discussed in detail here.

The characteristic of a surgical procedure is any information about the surgical procedure which affects a decision made by a participant of the surgical procedure. The type of surgical procedure (e.g. heart transplant) and the stage of the surgical procedure (e.g. the stage of making an incision or attaching a blood vessel during a heart transplant), as exemplified in FIGS. 2A and 4A are examples of characteristics of the surgical procedure. Other characteristics include, for example, a level of invasiveness of the surgical procedure (e.g. conventional surgery or key hole surgery), a level of risk of the surgical procedure (e.g. depending on physiological characteristics of the patient), the length of time taken for the surgical procedure so far and a level of competence of the participant (e.g. depending on measured physiological parameters of the participant which indicate a fatigue or experience level). The level of invasiveness may be defined, more generally, as the operative method used to carry out the specified surgical type.

Figure 6:
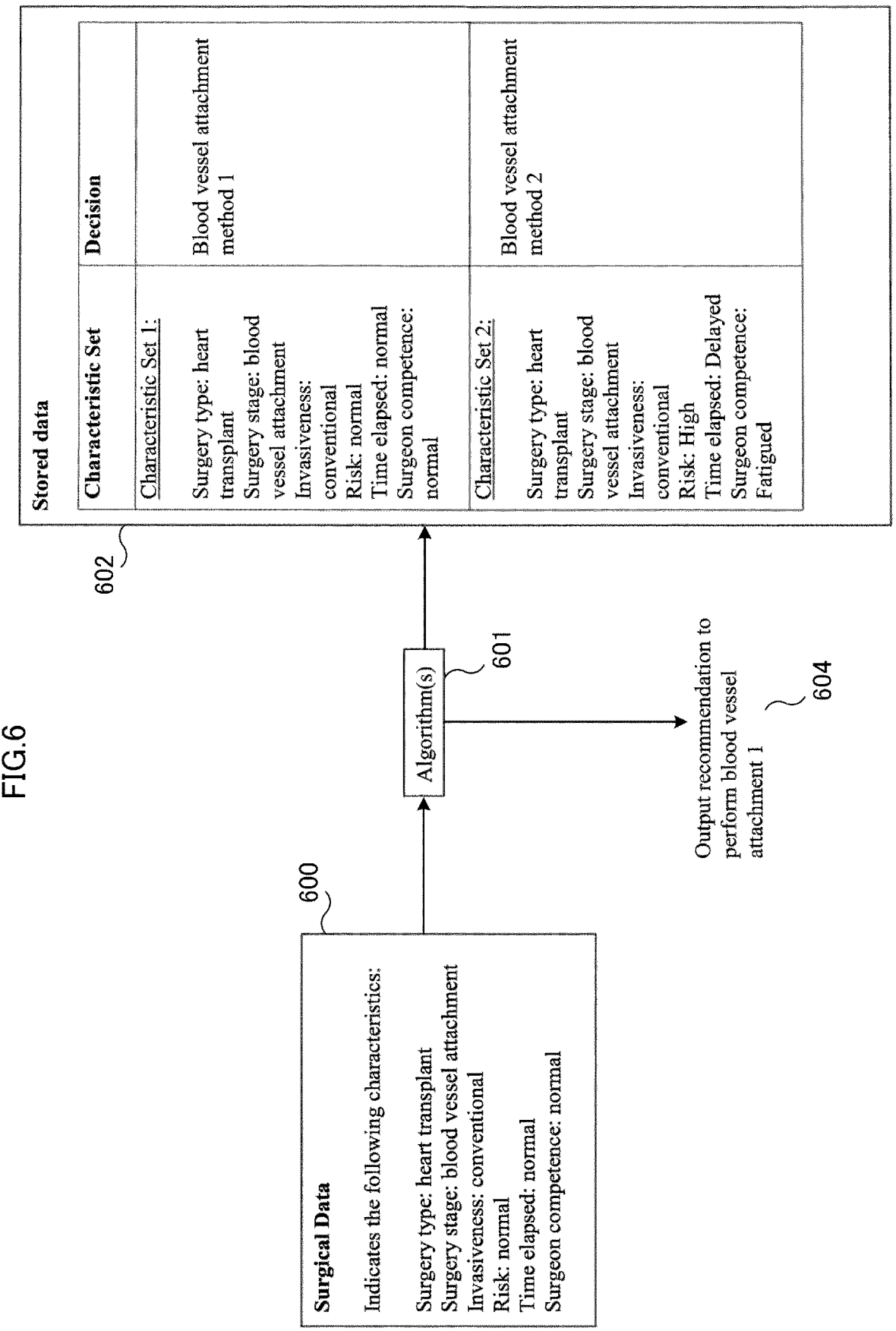
FIG. 6 schematically demonstrates the functionality of a personal AI, according to an embodiment.

An example of the generation of AI assistance information based on received surgical data of the current surgical procedure and the stored data and algorithm(s) of a personal AI is shown in FIG. 6. In this example, the surgical data 600 indicates, as characteristics of the current surgical procedure, that the surgery type is "heart transplant", the current stage of the surgery is "blood vessel attachment", the surgery invasiveness is "conventional" (as opposed to less invasive key hole surgery, for example), the risk level is "normal" (e.g. there is nothing about the patient's physiological condition which implies an increased level of risk), the time elapsed is "normal" (e.g. the surgery is not taking a longer or shorter time than usual) and the level of competence of the surgeon is "normal" (e.g. measured physiological parameters of the surgeon are not indicating a lack of experience or a level of fatigue which could negatively affect the surgery).

In an embodiment, the surgical data is in the form of raw data (e.g. a number indicative of a value of a measured parameter) generated by one or more devices used in the surgical procedure (e.g. devices 109 to 116). The raw data is then compared with one or more appropriate thresholds (e.g. via an algorithm of the personal AI) in order to determine one or more characteristics of the surgical procedure implied by the raw data. In another embodiment, the surgical data may be in a processed form (e.g. as processed by the device which generates the surgical data) which directly indicates one or more characteristics of the surgical procedure (e.g. the surgical data may comprise the information "normal" for the characteristic "risk" or "heart transplant" for the characteristic "surgery type").

The stored data 602 comprises a plurality of sets of characteristics of previous surgical procedures and an associated decision which was made by a surgeon to whom the personal AI belongs in response to those characteristics. In particular, there is a first set of characteristics (Characteristic Set 1) associated with a first decision (in which the surgeon opted to use a first blood vessel attachment method) and a second set of characteristics (Characteristic Set 2) associated with a second decision (in which the surgeon opted to use a second blood vessel attachment method). It will be appreciated that, although only two sets of characteristics are shown here (for ease of explanation), in reality, the stored data may contain many sets of characteristics and associated decisions based on data collected from many previous surgical procedures.

In this example, Characteristic Set 1 comprises the characteristics of the surgery type being "heart transplant", the current stage of the surgery being "blood vessel attachment", the surgery invasiveness being "conventional" (as opposed to less invasive key hole surgery, for example), the risk level being "normal" (e.g. there is nothing about the patient's physiological condition which implies an increased level of risk), the time elapsed being "normal" (e.g. the surgery is not taking a longer or shorter time than usual) and the level of competence of the surgeon being "normal" (e.g. measured physiological parameters of the surgeon are not indicating a lack of experience or a level of fatigue which could negatively affect the surgery). Characteristic Set 2 also comprises the characteristics of the surgery type being "heart transplant", the current stage of the surgery being "blood vessel attachment" and the surgery invasiveness being "conventional" (as opposed to less invasive key hole surgery, for example). However, Characteristic Set 2 also comprises the characteristics of the risk level being "high" (e.g. as a result of the patient's physiological condition implying an increased level of risk), the time elapsed being "delayed" (e.g. the surgery is taking a longer time than usual) and the level of competence of the surgeon is "fatigued" (e.g. measured physiological parameters of the surgeon indicate a level of fatigue which could negatively affect the surgery).

Characteristic Sets 1 and 2 therefore represent different surgical situations which warrant different action to be taken (i.e. different decisions to be made) by the surgeon. In this example, the second blood vessel attachment method is more appropriate for Characteristic Set 2, which indicates a surgical procedure in which a surgical error is more likely (due to the higher risk patient, the delayed surgery duration and the more highly fatigued surgeon). For example, the second blood vessel attachment method may be associated with a lower long term surgical success rate but may be quicker and/or easier to complete. The first blood vessel attachment method is more appropriate for Characteristic Set 1, which indicates a surgical procedure in which a surgical error is less likely (due to the normal risk patient, the normal surgery duration and the non-fatigued surgeon). For example, the first blood vessel attachment method may take longer and/or may be more difficult to complete but may have may be associated with a higher long term surgical success rate.

The surgical data acquired during the current surgical procedure and the stored data are provided to the algorithm(s) 601 of the personal AI for comparison. In this case, it will be appreciated that the characteristics indicated by the surgical data of the current surgical procedure most closely match those of Characteristic Set 1. This is determined by the algorithm(s) 106, which outputs assistance information 604 indicative of the decision "blood vessel attachment method 1" (associated with Characteristic Set 1). In this example, information indicative of the decision "blood vessel attachment method 1" is output as a recommendation to the surgeon carrying out the current surgical procedure.

It will be appreciated that this is a simplified example and that, in reality, the stored data may include a large number of combinations of different surgical characteristics recorded from a large number of previous surgical procedures and a large number of recorded decisions associated with those recorded surgical characteristics. In this case, the algorithm(s) 601 the personal AI may apply a suitable machine learning technique (e.g. neural network) in order to determine an appropriate decision based on the stored data (which acts as training data for the neural network) and the surgical data (which acts as an input to the neural network to be classified, the resulting classification being information indicative of a decision which is recommended to the surgeon).

Although, in the above-mentioned embodiments, the AI assistance information is provided in response to a request (e.g. vocal request) from the user (e.g. surgeon), in another embodiment, the AI assistance information may be provided automatically. For example, in response to the data processing apparatus 104 receiving surgical data from one or more of the devices 109 to 115, appropriate AI assistance information may be generated based on the received surgical data and provided to the user without the need for a user to make a request. In this case, the AI assistance information may be provided in a non-intrusive manner (e.g. visually with no audio), thereby providing the surgeon with AI assistance information that they may consult (e.g. by viewing a display of the user interface 115) if they wish but which does not unduly distract the surgeon. Because the surgeon has not made a request, the specific "expertise data" sought by the surgeon is not known. The automatically provided AI assistance information may therefore comprises a summarised version of AI assistance information for each type of expertise data based on the given characteristics of the surgery indicated by the surgical data. For example, if the surgery type/stage (as determined by the surgical data) is "heart transplant stage 2", then a summarised version of the AI assistance information for each of the expertise data "attachment equipment", "damage avoidance" and "attachment success" may be provided. In response to the surgeon then making a request for AI assistance information, the AI assistance information specific to expertise data indicated in the surgeon's request is provided to the surgeon in a more detailed format. In response to the surgeon's request, the AI assistance information requested by the surgeon may be provided in a more accessible manner (e.g. in a visual and audio format rather than just a visual format, as may be the case for automatically generated AI assistance information).

In an embodiment, as well as the AI assistance information comprising information indicative of a recommended decision from a personal AI based on the determined characteristic(s) of the current surgical procedure, the AI assistance information may also include relevant information gathered from other sources. Such additional information may include, for example, factual information about the current surgical procedure as found in medical journals, encyclopaedias or the like published on the internet. In the case of internet sources, the data processing apparatus 104 accesses the additional information via the communication interface 107 (which is able to exchange information with the server (not shown) on which the additional information is stored via the internet). The additional information may be provided in response to a request from the surgeon. For example, if the surgeon makes a request containing information which does not obviously correlate with relevant "expertise data" for the current surgical procedure type/ stage, then the data processing apparatus 104 may seek an answer to the surgeon's request using additional information such as that available on the internet. To enable this functionality, the data processing apparatus 104 is configured to run an internet service-based virtual assistant capable of natural language processing in parallel with the one or more personal AIs already discussed.

Some embodiments of the present technique are defined by the following numbered clauses:

(1)
A surgical support system including:
a surgical data generating apparatus operable to generate surgical data associated with a surgical procedure; and
a data processing apparatus operable to:
determine artificial intelligence (AI) assistance information using the generated surgical data; and
provide the determined AI assistance information to a user.

(2)
A surgical support system according to clause (1), wherein the AI assistance information is determined and provided to the user in response to a request received from the user for AI assistance information.

(3)
A surgical support system according to clause (1), wherein the AI assistance information is determined and provided to the user in response to the data processing apparatus receiving the generated surgical data.

(4)
A surgical support system according to clause (3), wherein:
the request for AI assistance information comprises expertise data indicative of a predetermined area of expertise; and
the data processing apparatus is operable to determine the AI assistance information using the expertise data.

(5)
A surgical support system according to any preceding clause, including a user interface device operable to provide the determined AI assistance information to the user.

(6)
A surgical support system according to clause (4), wherein the user interface device includes a head mountable display (HMD) wearable by the user and operable to display an augmented reality (AR) image representative of the determined AI assistance information to the user.

(7)
A surgical support system according to clause (1), wherein the generated surgical data is indicative of a characteristic of the surgical procedure.

(8)
A surgical support system according to any preceding clause, wherein:
the data processing apparatus is operable to generate the AI assistance information using one or more of a plurality of AI assistants, each AI assistant comprising data associated with a respective second user and recorded during a previous surgical procedure and instructions for performing one or more algorithms using the data associated with that second user to predict a decision that second user would make; and
the determination of the AI assistance information comprises selecting the one or more of the plurality of AI assistants.

(9)
A surgical support system according to clause (8), wherein the selection of the one or more of the plurality of AI assistants comprises determining, for each of a plurality of candidate AI assistants, one or more scores each indicative of predetermined characteristic of that candidate AI assistant and selecting the one or more of the plurality of AI assistants using the one or more scores.

(10)

A surgical support system according to clause (9), wherein the one or more scores include a score indicative of a level of trust between the user making the request for AI assistance information and the second user associated with each respective candidate AI assistant.

(11)

A surgical support system according to clause (9) or (10), wherein the one or more scores include a score indicative of a level of competence of the second user associated with each respective candidate AI assistant.

(12)

A surgical support system according to clause (9) or (10), wherein the one or more scores include a score indicative of a level of training quality of the data comprised within each respective candidate AI assistant.

(13)

A surgical support system according to any one of clauses (8) to (12), wherein the selection of the one or more of the plurality of AI assistants includes determining a preferred one or more of the plurality of AI assistants for each of a plurality of members of a surgical team performing the surgical procedure and determining a most preferred one or more of the plurality of AI assistants amongst the plurality of members of the surgical team as the one or more of the plurality of AI assistants.

(14)

A surgical support system according to any preceding clause, wherein the AI assistance information includes information obtained from an internet service.

(15)

A data processing apparatus for a surgical support system, the surgical support system including a surgical data generating apparatus operable to generate surgical data associated with a surgical procedure, wherein the data processing apparatus includes circuitry configured to:
receive the generated surgical data;
determine artificial intelligence (AI) assistance information using the generated surgical data; and
provide the determined AI assistance information to a user.

(16)

A method of operating a surgical support system, the surgical support system including a surgical data generating apparatus operable to generate surgical data associated with a surgical procedure, wherein the method includes:
receiving the generated surgical data;
determining artificial intelligence (AI) assistance information using the generated surgical data; and
providing the determined AI assistance information to a user.

(17)

A program for controlling a computer to perform a method according to clause (16).

(18)

A storage medium storing a program according to clause (17).

Numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

REFERENCES

NPL 1: Mezger U, Jendrewski C, Bartels M. Navigation in surgery. Langenbeck's Archives of Surgery. 2013; 398(4): 501-514. doi:10.1007/s00423-013-1059-4.

The invention claimed is:

1. A surgical support system comprising:
a surgical data generating circuit configured to generate surgical data associated with a surgical procedure and output generated surgical data, wherein the generated surgical data includes data regarding a characteristic of a surgical procedure to be performed; and
a data processing circuit configured to:
generate the AI assistance information using one or more of a plurality of AI assistants, each AI assistant including data associated with a respective second user and recorded during a previous surgical procedure and instructions for performing one or more algorithms using the data associated with that second user to predict a decision that second user would make;
select the one or more of the plurality of AI assistants;
determine artificial intelligence (AI) assistance information using the generated surgical data received from the surgical data generating circuit and the one or more of the plurality of AI assistants; and
provide the determined AI assistance information to a user and to a surgical robot to control the surgical robot in accordance with determined AI assistance information regarding the characteristic of the surgical procedure to be performed.

2. A surgical support system according to claim 1, wherein the AI assistance information is determined and provided to the user in response to a request received from the user for AI assistance information.

3. A surgical support system according to claim 1, wherein the AI assistance information is determined and provided to the user in response to the data processing apparatus receiving the generated surgical data.

4. A surgical support system according to claim 3, wherein:
the request for AI assistance information comprises expertise data indicative of a predetermined area of expertise; and
the data processing apparatus is operable to determine the AI assistance information using the expertise data.

5. A surgical support system according to claim 4, wherein the user interface includes a head mountable display (HMD) wearable by the user and operable to display an augmented reality (AR) image representative of the determined AI assistance information to the user.

6. A surgical support system according to claim 1, comprising a user interface to provide the determined AI assistance information to the user.

7. A surgical support system according to claim 1, wherein the data processing circuit is configured to select the one or more of the plurality of AI assistants by determining, for each of a plurality of candidate AI assistants, one or more scores each indicative of predetermined characteristic of that candidate AI assistant and selecting the one or more of the plurality of AI assistants using the one or more scores.

8. A surgical support system according to claim 7, wherein the one or more scores comprise a score indicative of a level of trust between the user making the request for AI assistance information and the second user associated with each respective candidate AI assistant.

9. A surgical support system according to claim 7, wherein the one or more scores comprise a score indicative of a level of competence of the second user associated with each respective candidate AI assistant.

10. A surgical support system according to claim 7, wherein the one or more scores comprise a score indicative of a level of training quality of the data comprised within each respective candidate AI assistant.

11. A surgical support system according to claim 1, wherein the data processing circuit is configured to select the one or more of the plurality of AI assistants includes determining a preferred one or more of the plurality of AI assistants for each of a plurality of members of a surgical team performing the surgical procedure and determining a most preferred one or more of the plurality of AI assistants amongst the plurality of members of the surgical team as the one or more of the plurality of AI assistants.

12. A surgical support system according to claim 1, wherein the AI assistance information comprises information obtained from an internet service.

13. A data processing apparatus for a surgical support system, the surgical support system comprising a surgical data generating apparatus operable to generate surgical data associated with a surgical procedure, wherein the data processing apparatus comprises circuitry configured to:
receive the generated surgical data;
generate the AI assistance information using one or more of a plurality of AI assistants, each AI assistant including data associated with a respective second user and recorded during a previous surgical procedure and instructions for performing one or more algorithms using the data associated with that second user to predict a decision that second user would make;
select the one or more of the plurality of AI assistants;
determine artificial intelligence (AI) assistance information using the generated surgical data and the one or more of the plurality of AI assistants; and
provide the determined AI assistance information to a user and to a surgical robot to control the surgical robot in accordance with determined AI assistance information regarding the characteristic of the surgical procedure to be performed.

14. A data processing apparatus according to claim 13, wherein the circuitry is configured to select the one or more of the plurality of AI assistants by determining, for each of a plurality of candidate AI assistants, one or more scores each indicative of predetermined characteristic of that candidate AI assistant and selecting the one or more of the plurality of AI assistants using the one or more scores.

15. A data processing apparatus according to claim 13, wherein the circuitry is configured to select the one or more of the plurality of AI assistants includes determining a preferred one or more of the plurality of AI assistants for each of a plurality of members of a surgical team performing the surgical procedure and determining a most preferred one or more of the plurality of AI assistants amongst the plurality of members of the surgical team as the one or more of the plurality of AI assistants.

16. A method of operating a surgical support system, the surgical support system comprising a surgical data generating apparatus operable to generate surgical data associated with a surgical procedure, wherein the method comprises:
receiving the generated surgical data;
generating AI assistance information using one or more of a plurality of AI assistants, each AI assistant including data associated with a respective second user and recorded during a previous surgical procedure and instructions for performing one or more algorithms using the data associated with that second user to predict a decision that second user would make;
selecting the one or more of the plurality of AI assistants;
determining artificial intelligence (AI) assistance information using the generated surgical data and the one or more of the plurality of AI assistants; and
providing the determined AI assistance information to a user and to a surgical robot to control the surgical robot in accordance with determined AI assistance information regarding the characteristic of the surgical procedure to be performed.

17. An apparatus comprising:
a non-transitory storage medium storing a program; and
a processing circuit configured to perform a method according to claim 16.

18. A non-transitory storage medium having computer readable instructions that when executed by circuitry cause the circuitry to execute the method according to claim 16.

19. A method according to claim 16, wherein selecting the one or more of the plurality of AI assistants includes determining, for each of a plurality of candidate AI assistants, one or more scores each indicative of predetermined characteristic of that candidate AI assistant and selecting the one or more of the plurality of AI assistants using the one or more scores.

20. A method according to claim 16, wherein selecting the one or more of the plurality of AI assistants includes determining a preferred one or more of the plurality of AI assistants for each of a plurality of members of a surgical team performing the surgical procedure and determining a most preferred one or more of the plurality of AI assistants amongst the plurality of members of the surgical team as the one or more of the plurality of AI assistants.

* * * * *